United States Patent [19]

Kimura

[11] Patent Number: 5,286,842
[45] Date of Patent: Feb. 15, 1994

[54] PROCESS FOR PRODUCING A BIODEGRADABLE POLYMER

[75] Inventor: Yoshiharu Kimura, Omihachiman, Japan

[73] Assignee: Mitsubishi Kasei Corporation, Tokyo, Japan

[21] Appl. No.: 906,675

[22] Filed: Jun. 30, 1992

[30] Foreign Application Priority Data

Jul. 1, 1991 [JP] Japan .................. 3-160695
Jul. 1, 1991 [JP] Japan .................. 3-160696
Jul. 1, 1991 [JP] Japan .................. 3-160698

[51] Int. Cl.$^5$ .................. C08G 63/08
[52] U.S. Cl. .................. 528/354; 549/267
[58] Field of Search .................. 528/354; 549/267

[56] References Cited

U.S. PATENT DOCUMENTS 3,297,033 1/1967 Schmitt et al. .
4,590,005 5/1986 Shanzer et al. .

FOREIGN PATENT DOCUMENTS 0471364 2/1992 European Pat. Off. .
1277862 4/1969 Fed. Rep. of Germany .
61-236820 10/1986 Japan .
1-103622 4/1989 Japan .
2-3415 1/1990 Japan .
02040343 2/1990 Japan .
2-209918 8/1990 Japan .
4-3763 1/1992 Japan .

OTHER PUBLICATIONS

Journal American Chem. Society, 105(12) (1983) Lifson, Shcheinor, pp. 3866-3875.

Primary Examiner—John Kight, II
Assistant Examiner—T. Mosley
Attorney, Agent, or Firm—Oblon, Spivak, McClelland, Maier & Neustadt

[57] ABSTRACT

A process for producing a biodegradable polymer, which comprises subjecting a cyclic compound of the following formula (1) or (2) to ring opening polymerization:

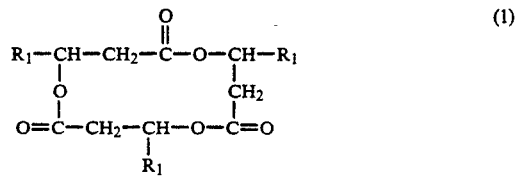

wherein $R_1$ is a $C_{1-10}$ alkyl group,

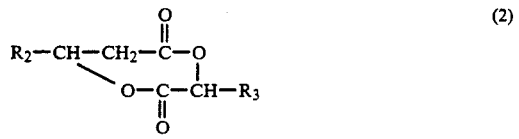

wherein $R_2$ is a $C_{1-10}$ alkyl group, and $R_3$ is a hydrogen atom or a $C_{1-10}$ alkyl group.

6 Claims, 5 Drawing Sheets

PROCESS FOR PRODUCING A BIODEGRADABLE POLYMER

The present invention relates to a novel process for producing a biodegradable polymer or a polymer for medical use and novel starting materials for the polymer. Further, it relates to processes for producing the starting materials.

Recently, attention has been drawn to biodegradable polymers in view of a global environmental problem.

Polymers produced by microorganisms are degradable by microorganisms in the earth or sea. Accordingly, a process for producing polymers by a fermentation method is being studied. For example, Japanese Unexamined Patent Publication No. 269989/1988 discloses a synthesis of a polyhydroxybutyrate by a fermentation method. However, this method has a problem of costs and has not yet been used for mass production. Further, a synthesis of a biodegradable polymer using lactic acid or glycolic acid as the starting material, is being studied. However, it has not been possible to obtain a polymer of a high molecular weight by directly polymerizing such a hydroxy aliphatic carboxylic acid or its ester. Under the circumstances, it has been proposed to produce a polymer of a high molecular weight by subjecting a cyclic dimer such as a lactide or glycolide to ring opening polymerization. For example, Japanese Unexamined Patent Publication No. 3415/1990 proposes a synthesis of an α-oxyacid polymer by ring opening polymerization of the following compound:

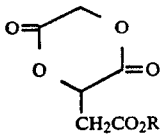

Further, Japanese Unexamined Patent Publication No. 280220/1987 proposes a process which comprises reacting a polylactide or a polyglycolide with a dichloride compound.

It is an object of the present invention to provide a process for producing a biodegradable polymer of a high molecular weight constantly at low costs without using a fermentation method.

As a result of an extensive research, it has been found possible to accomplish the object by using novel cyclic monomers as the starting material.

That is, the present invention provides a process for producing a biodegradable polymer, which comprises subjecting a novel cyclic compound of the following formula (1) or (2) to ring opening polymerization:

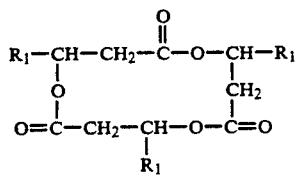

wherein $R_1$ is a $C_{1-10}$ alkyl group,

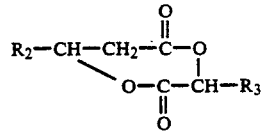

wherein $R_2$ is a $C_{1-10}$ alkyl group, and $R_3$ is a hydrogen atom or a $C_{1-10}$ alkyl group.

Figure 1:
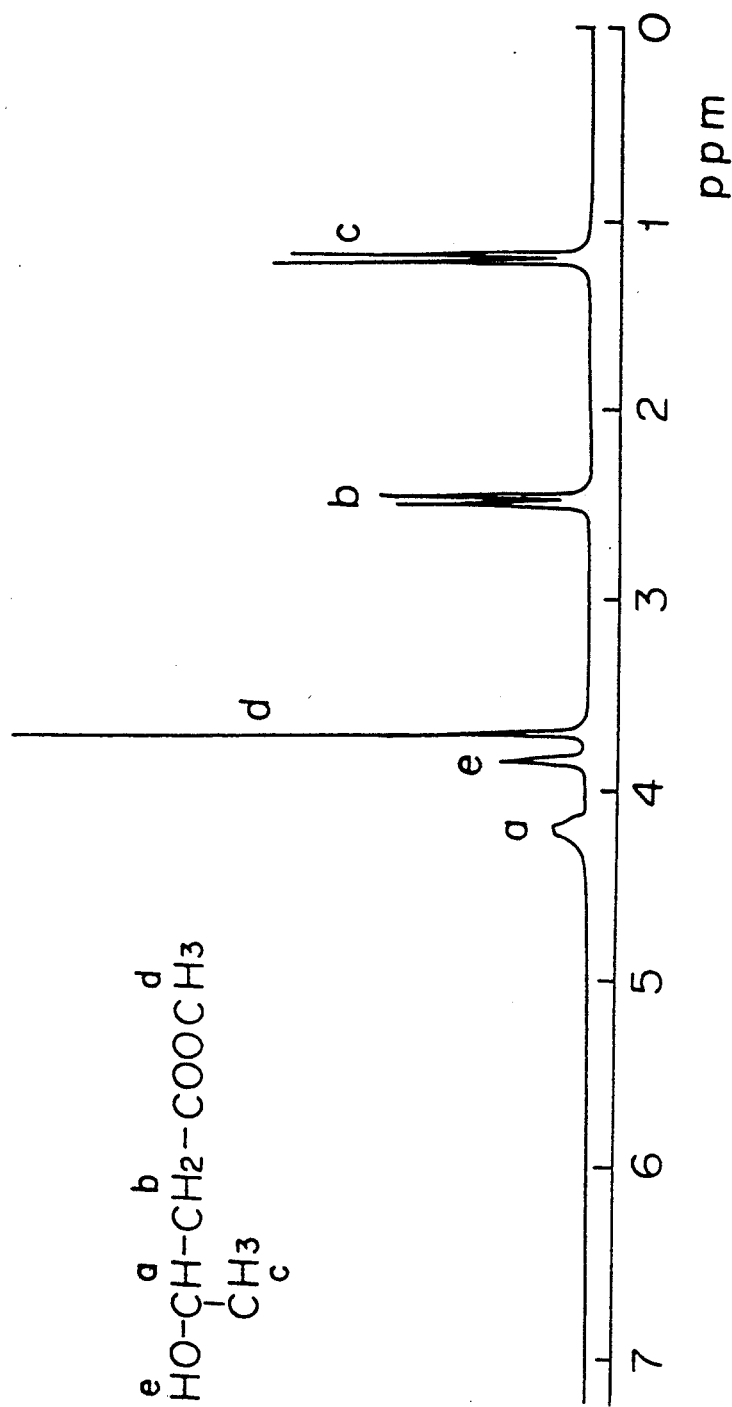
FIG. 1 is the $^1$H-NMR spectrum of methyl 3-hydroxybutyrate.

Now, the present invention will be described in detail with reference to the preferred embodiments.

Firstly, the ring opening polymerization of the compound of the formula (1) will be described.

The compound of the formula (1) can be obtained by dissolving a compound of the following formula (3):

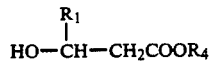

wherein $R_1$ is as defined above, and $R_4$ is a $C_{1-10}$ alkyl group in an organic solvent, refluxing the solution together with an ester exchange catalyst and then removing the solvent by e.g. distillation to isolate the compound of the formula (1).

The compound of the formula (3) may be any compound so long as it is represented by the formula (3). Specific examples may be methyl 3-hydroxybutyrate, methyl 3-hydroxyvalerate, ethyl 3-hydroxybutyrate, methyl 3-hydroxycaproate, ethyl 3-hydroxycaproate and ethyl 3-hydroxycaprate. Particularly preferred is methyl 3-hydroxybutyrate. The compound of the formula (3) is a compound having an asymmetric carbon atom, and one of the optical isomers may be used, as the case requires.

As the organic solvent, any solvent may be employed so long as it is capable of dissolving the compound of the formula (1). Specific examples include toluene, xylene, benzene, chloroform, chlorobenzene, o-dichlorobenzene, ethanol, dioxane, dimethylacetamide, dimethylformamide, N-methylpyrrolidone, tetrahydrofuran, dibutyl ether, n-hexane, n-pentane, and acetonitrile. Among them, a compound having a boiling point of not higher than 200° C. and capable of being azeotripically distilled in water, is preferred. Particularly preferred is toluene.

The amount of the solvent is not particularly limited. For the separation step, however, the amount is preferably not more than 50 times of the starting material.

As the ester exchange catalyst, tetra-n-butyl titanate, zinc acetate, antimony trioxide, calcium acetate, dibutyltin oxide, dibutyltin dichloride, tetrabutyltin, dibutyltin dilaurate, tin dichloride, tin tetrachloride, dioctyltin diacetate, stannous acetate or stannic acetate may be mentioned. Preferred is a catalyst of tin, titanium or antimony type. More preferred is a catalyst of tin-type. The most preferred catalyst is a dialkyltin oxide such as dibutyltin oxide.

Removal of the solvent may be conducted by a conventional separation method. Usually, a distillation method is simple and convenient. Purification of the compound of the formula (1) can be conducted by distillation under vacuum after the removal of the solvent or by recrystallization from an organic solvent such as petroleum ether.

The ring opening polymerization reaction of the cyclic compound of the formula (1) according to the present invention is conducted in the presence of a catalyst. Specific examples of such catalyst include a tin compound, a zinc compound, an aluminum compound, an antimony compound and a titanium compound. Particularly preferred is a tin compound, an alkylaluminum-hydrogen catalyst or a diethylzinc-hydrogen catalyst.

The polymerization reaction may be conducted in the presence or absence of a solvent. When a solvent is to be used, any solvent may be employed so long as it is capable of dissolving the compound of the formula (1) and which does not inactivate the catalyst. Specific examples include tetrahydrofuran, dichloromethane, chloroform, o-dichlorobenzene and dioxane.

The optimum conditions for the polymerization vary depending upon the catalyst. However, the polymerization is conducted usually within a temperature range of from 0° to 300° C., preferably from 20° to 200° C.

In the compound of the formula (1), $R_1$ is a $C_{1-10}$ alkyl group. $R_1$ is preferably methyl, ethyl, isopropyl, n-propyl or n-butyl. Particularly preferred is the case where $R_1$ is methyl. Specifically, there may be mentioned 1,5,9-trioxa-2,6,10-trimethylcyclododeca-4,8,12-trione,
1,5,9-trioxa-2,6,10-triethylcyclododeca-4,8,12-trione,
1,5,9-trioxa-2,6,10-triisopropylcyclododeca-4,8,12-trione and
1,5,9-trioxa-2,6,10-tri-n-hexylcyclododeca-4,8,12-trione, Among them, 1,5,9-trioxa-2,6,10-trimethylcyclododeca-4,8,12-trione is preferred. An optically active compound is more preferred.

Now, the ring opening polymerization of the compound of the formula (2) will be described.

The compound of the formula (2) can be prepared by reacting a compound of the formula (4):

HO—CHR₂—CH₂COOH            (4)

wherein $R_2$ is as defined above with respect to the formula (2), with a compound of the formula (5):

X—CHR₃—CO—Y            (5)

wherein $R_3$ is as defined above with respect to the formula (2), and each of X and Y is a halogen atom, to form a compound of the formula (6):

(6)

wherein $R_2$, $R_3$ and X are as defined above, and then subjecting the compound of the formula (6) to a ring closure reaction to obtain a cyclic compound of the formula (2).

This process will be described in further detail.

The compound of the formula (4) and the compound of the formula (5) are dissolved in a solvent and then reacted in the presence of an amine compound to obtain the above compound of the formula (6). Then, the compound of the formula (6) is treated with alkali for the ring closure reaction to obtain a cyclic compound of the formula (2) of the present invention.

The compound of the formula (4) to be used in the present invention, is not particularly limited. However, specific examples include 3-hydroxybutyric acid, 3-hydroxyvaleric acid, a 3-hydroxycaproic acid, and 3-hyroxycaprylic acid. Particularly preferred is 3-hydroxybutyric acid.

The compound of the formula (5) is not particularly limited. However, the one wherein X is Br and Y is Cl, is particularly preferred. Specific examples include α-bromoacetyl chloride, α-bromopropionic acid chloride, α-chloroacetyl chloride, α-bromobutyric acid chloride and α-bromocaprylic acid chloride. Particularly preferred is α-bromoacetyl chloride. The ratio of the amount of the compound of the formula (4) to the amount of the compound of the formula (5) is within a range of from 1:10 to 10:1, more preferably from 1:2 to 2:1, by an equivalent ratio.

A solvent for the reaction of the compound of the formula (4) with the compound of the formula (5), may be any solvent so long as it is capable of dissolving both compounds. Specifically, it may be an ether such as diethyl ether, tetrahydrofuran, dioxane or dibutyl ether, a hydrocarbon such as toluene, xylene or n-hexane, dimethylacetamide, dimethylformamide, N-methylpyrrolidone or acetonitrile. As the amine compound, a tertiary amine such as triethylamine or tributylamine, or an aromatic amine such as pyridine or quinoline, may be employed. Particularly preferred is triethylamine.

The amount of the amine is preferably at least equal to or up to five times the amount of the compound of the formula (2). The reaction temperature is usually from 10° to 100° C., preferably from 0° to 40° C., and the reaction time is usually from 30 minutes to 50 hours, preferably from 5 to 20 hours. As the alkali compound to be used for the ring closure reaction of the compound of the formula (6), sodium hydrogencarbonate, sodium carbonate, potassium carbonate, sodium hydroxide or potassium hydroxide may be employed. Particularly preferred is sodium hydrogencarbonate.

The cyclic compound of the present invention contains an asymmetric carbon atom. Therefore, it can be made an optically active cyclic compound, as the case requires.

The polymerization method may be the same as used for the ring opening polymerization of the compound of the formula (1).

Now, the present invention will be described in further detail with reference to Examples. However, it should be understood that the present invention is by no means restricted by such specific Examples.

EXAMPLE 1

Preparation of 1,5,9-trioxa-2,6,10-trimethylcyclododeca-4,8,12-trione

To a solution containing 30 g of methyl 3-(S)-hydroxybutyrate in 500 ml of toluene, 1.9 g of dibutyltin (IV) oxide was added, and the mixture was refluxed for 48 hours. After the reaction, toluene was distilled under reduced pressure. The obtained product was distilled under vacuum (about 10⁻³ mmHg) by means of a glass tube oven, and a fraction of from 120° to 150° C. was recrystallized from petroleum ether. The amount obtained after the recrystallization was 2.5 g. The obtained product was white transparent rhombic crystals.

Figure 2:
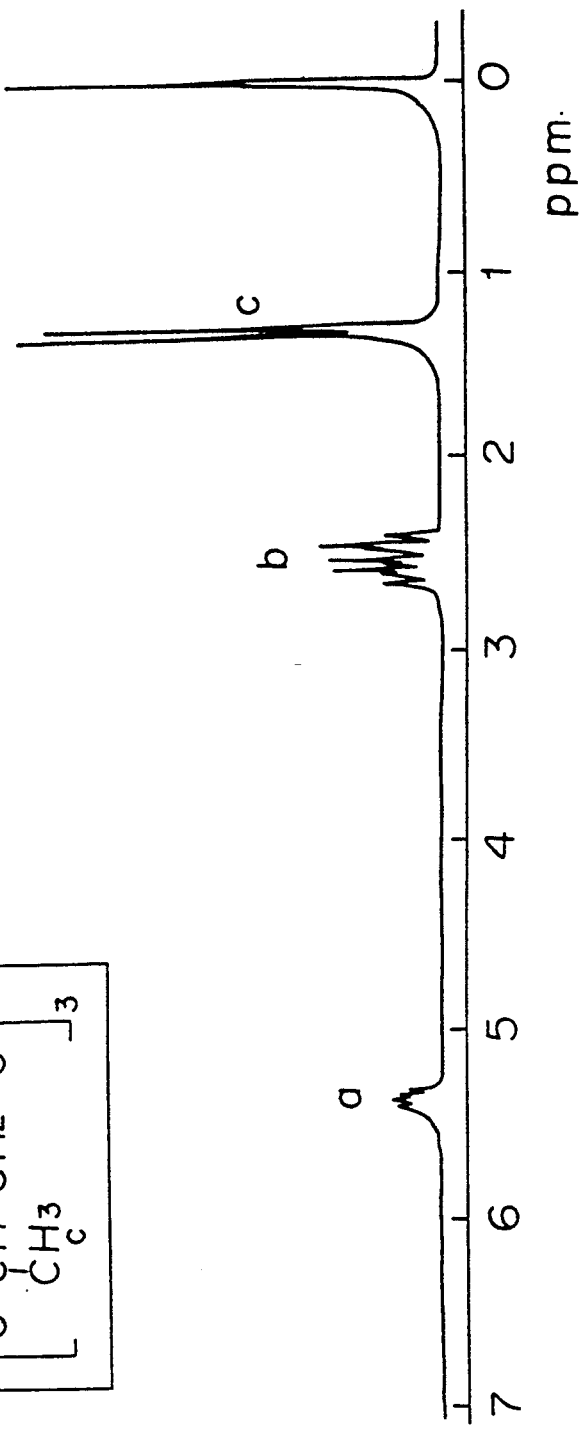
FIG. 2 is the $^1$H-NMR spectrum of a cyclic trimer of the 3-hydroxybutyrate.

FIG. 1 shows the $^1$H-NMR spectrum of methyl 3-hydroxybutyrate, and FIG. 2 shows the $^1$H-NMR spectrum of the cyclic trimer thereof. The peaks for $CH_3$ and OH observed at about 3.7 ppm and 3.8 ppm with respect to methyl 3-hydroxybutyrate, disappeared, and the peak for CH at about 4.2 ppm shifted to 5.3 ppm, and the doublet for $CH_2$ at 2.5 ppm was disintegrated into a multiplet with the cyclic trimer. The molecular weight was measured by the mass spectrum and found to be 258, whereby formation of the cyclic timer was confirmed.

EXAMPLE 2

Figure 3:
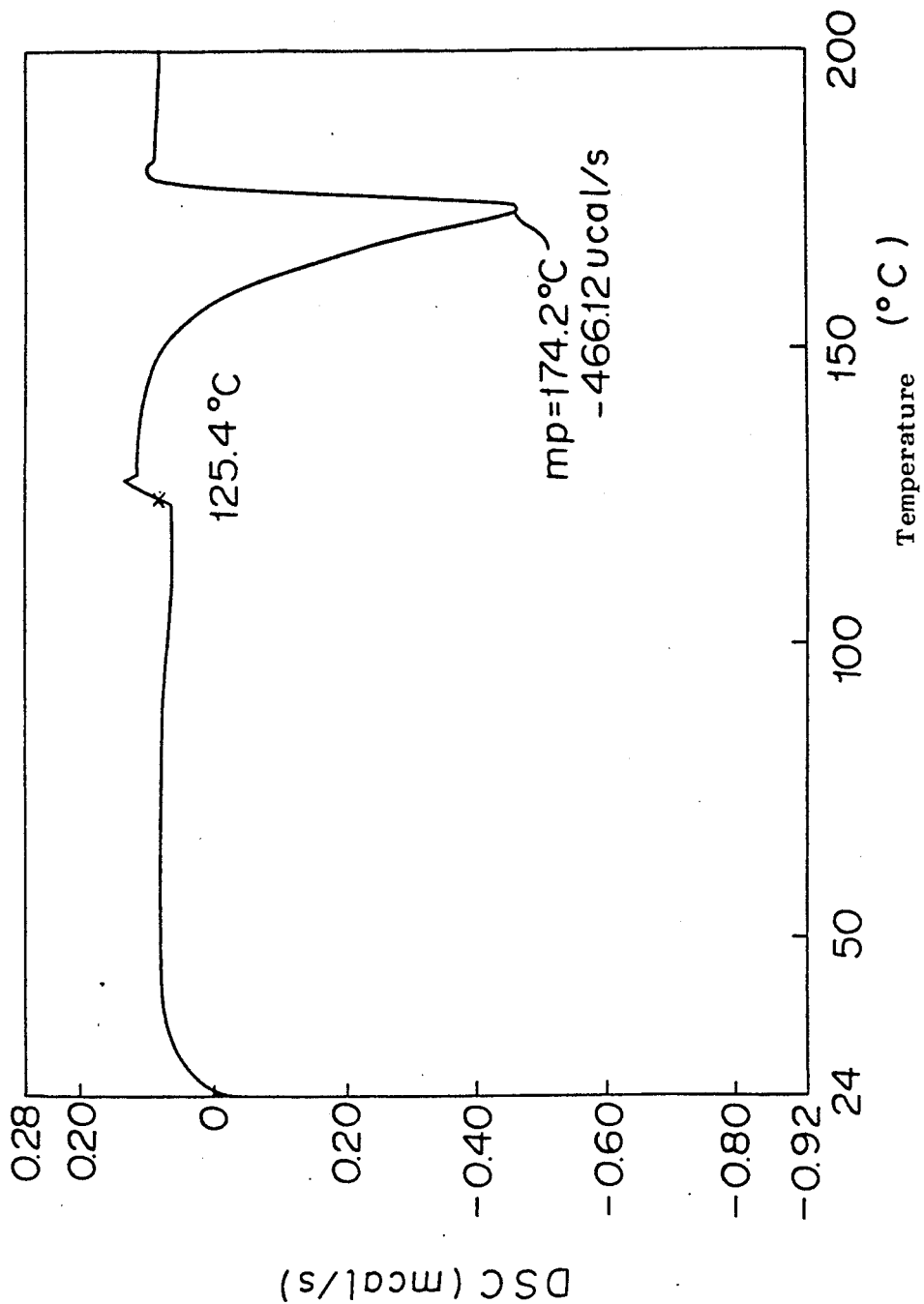
FIG. 3 shows the results of measurement of the melting point of the polymer obtained in Example 2 by a differential scanning calorimeter.
Figure 4:
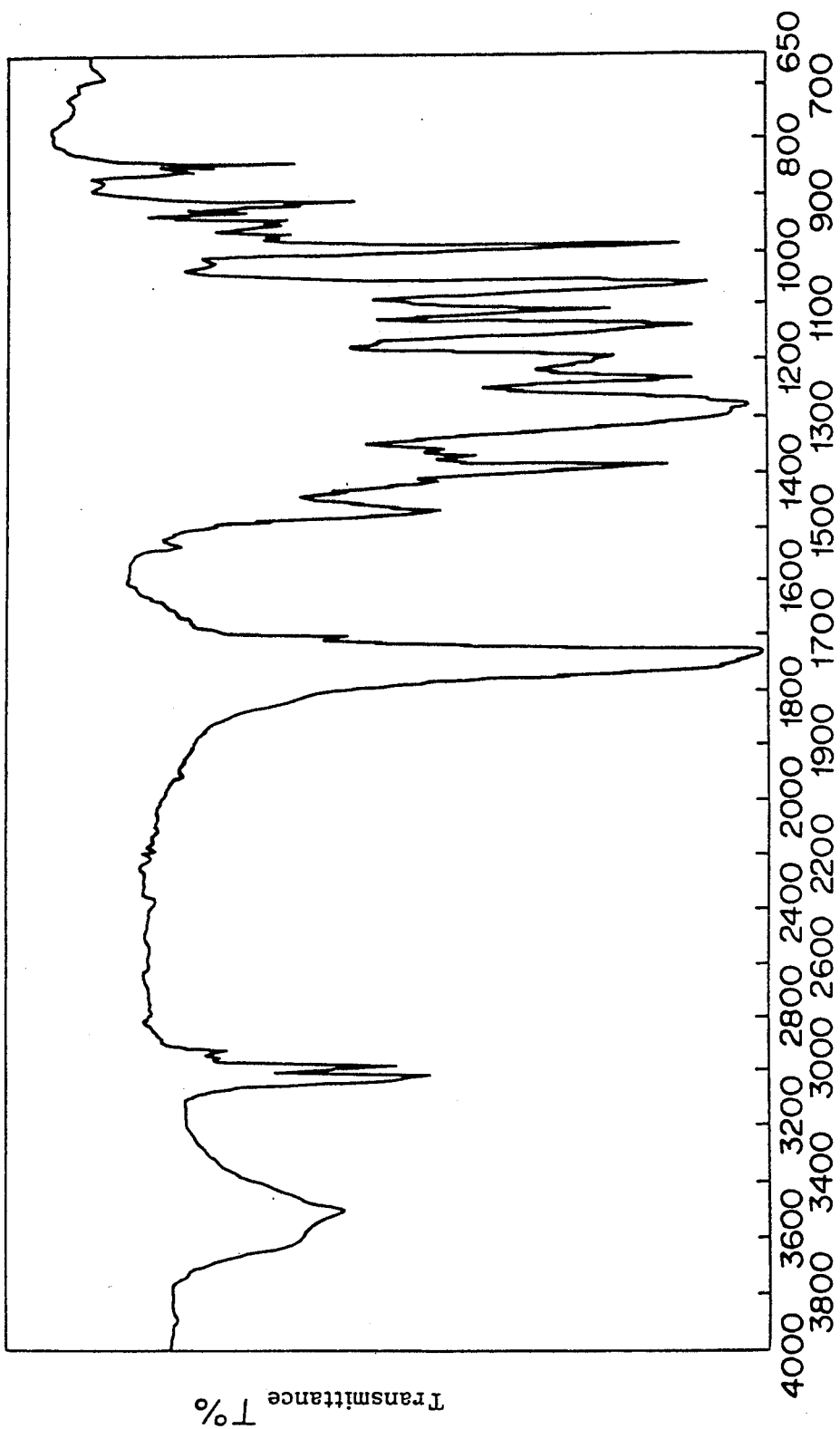
FIG. 4 is the IR spectrum of the polymer obtained in Example 2.

1.0 g of the cyclic oligomer prepared in Example 1 (1,5,9-trioxa-2,6,10-trimethylcyclododeca-4,8,12-trione) was put into a glass tube, and 1 ml of a toluene solution of tin octylate (concentration: 1% by weight) was added thereto, followed by deaeration and drying. Then, the glass reaction tube was sealed in a nitrogen atmosphere and heated at 150° C. for 5 hours. To the solid product thereby obtained, 30 ml of chloroform was added, and the mixture was stirred. The precipitate was collected by filtration and dried. The melting point of the obtained polymer was measured by a differential scanning calorimeter (DSC) (MacSience DSC-3300) and found to be 174.2° C. Further, absorption by carbonyl was confirmed by the infrared absorption spectrum (IR spectrum), whereby formation of the polymer of 3-oxybutyrate was confirmed. The DSC results of the polymer are shown in FIG. 3, and the IR spectrum is shown in FIG. 4.

EXAMPLE 3

Into a 200 cc round bottom flask, 1.0 g of the cyclic oligomer prepared in Example 1 and 2 ml of 1,4-dioxane were introduced, and 20 ml of triethylaluminum was added while stirring the mixture by a magnetic stirrer at room temperature. Then, stirring was continued at 60° C. for 5 hours for polymerization. During this period, the system became turbid.

After completion of the reaction, the reaction product was poured into a large amount of diethyl ether, and the precipitate was collected by filtration and dried. This product was ascertained to be a polymer having the same structural units as in Example 2 by IR.

EXAMPLE 4

Preparation of 3-($\alpha$-bromoacetoxy)butyric acid 5 g (0.048 mol) of 3-hydroxybutyric acid and 0.062 mol of bromoacetyl chloride were dissolved in 100 ml of diethyl ether. This solution was stirred in an ice bath, and while maintaining the solution at a level of not higher than 5° C., 20 ml of diethyl ether containing 5.35 g (0.053 mol) of triethylamine was dropwise added over a period of 30 minutes. After the dropwise addition, the mixture was stirred at room temperature for 10 hours. Then, triethylamine hydrochloride was filtered off from the reaction solution, and the filtrate was washed three times with distilled water. The ether solution thereby obtained was dried over anhydrous sodium sulfate, and then diethyl ether was distilled off. As a result, a slightly yellow desired compound was obtained in a yield of 70%.

EXAMPLE 5

Figure 5:
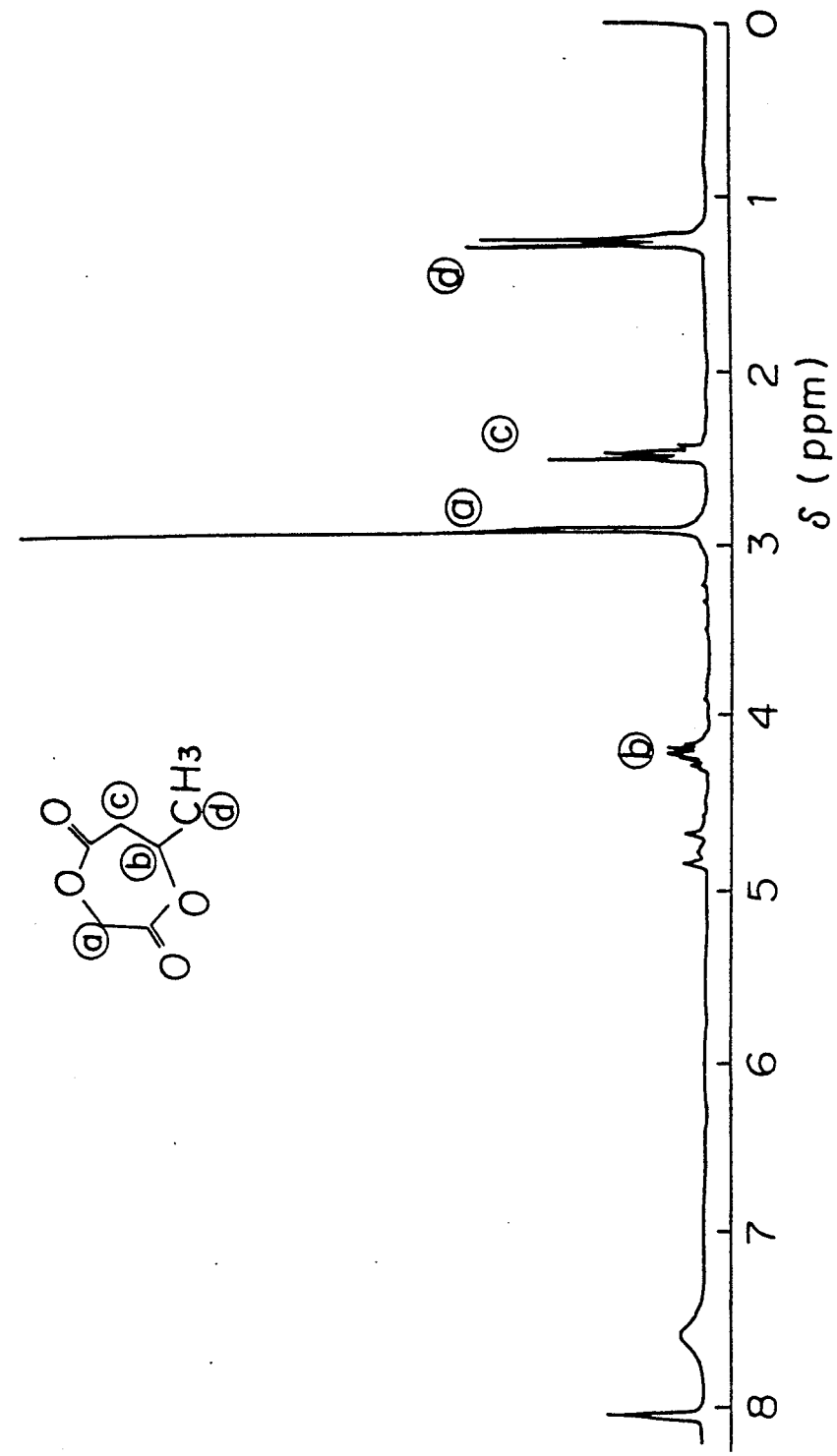
FIG. 5 is the $^1$H-NMR spectrum of the cyclic compound obtained in Example 5.

Preparation of 7-methyl-1,4-dioxepan-2,5-dione 4 g (0.048 mol) of sodium carbonate was mixed with 750 ml of dimethylformamide, while vigorously stirring the mixture at room temperature, 50 ml of a dimethylformamide solution containing 7 g (0.031 mol) of 3-($\alpha$-bromoacetoxy)butyric acid, was dropwise added over a period of 10 hours. After completion of the dropwise addition, stirring was continued at the same temperature for 20 hours. The reaction solution was filtered to remove an insoluble white precipitate, and then dimethylformamide was distilled off under reduced pressure. The residual turbid solution was dissolved in acetone, and insoluble matters were filtered off. Then, acetone was distilled off to obtain a product. The $^1$H-NMR spectrum of the product is shown in FIG. 5. In the Figure, symbols a to d have the following meanings.

a: 2.90 ppm, singlet,
b: 4.24 ppm, multiplet,
c: 2.70 ppm, multiplet,
d: 1.26 ppm doublet.

By the process for producing a biodegradable polymer by the ring opening polymerization of the compound of the formula (1) of the present invention, it is possible to produce a polyester having 3-hydroxybutyrate units (hereinafter referred to simply as 3HB) at low costs as compared with the fermentation method, and yet a high molecular weight as compared with the direct polymerization of the 3HB monomer, can be attained.

Further, a copolymer of 3HB with an optional monomer can readily be prepared. Therefore, this process is useful as a substitute for the fermentation method.

Further, according to the process for producing a biodegradable polymer by the ring opening polymerization of the compound of the formula (2) of the present invention, the obtained biodegradable polymer is excellent in the flexibility and elongation. Further, it is thereby possible to produce a copolymer wherein the constituting units are alternately arranged rather than a block fashion as compared with the direct polymerization of monomers of glycolic acid and 3HB, and such a copolymer is excellent also in the mechanical properties and thus is useful for e.g. surgical sutures.

I claim:

1. A process for producing a biodegradable polymer, which comprises subjecting a cyclic compound of the following formula (1) or (2) to ring opening polymerization:

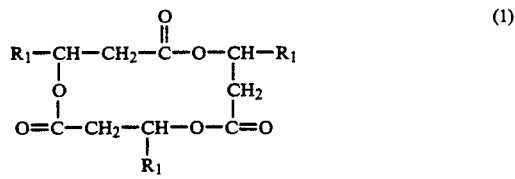

wherein $R_1$ is a $C_{1-10}$ alkyl group,

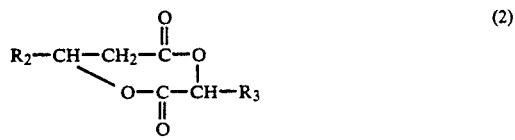

wherein $R_2$ is a $C_{1-10}$ alkyl group, and $R_3$ is a hydrogen atom or a $C_{1-10}$ alkyl group.

2. A cyclic compound of the formula (1):

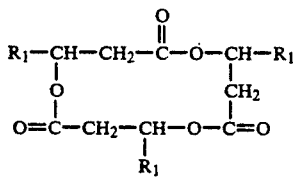
(1)

wherein $R_1$ is a $C_{1-10}$ alkyl group.

3. A process for producing a cyclic compound of the formula (1):

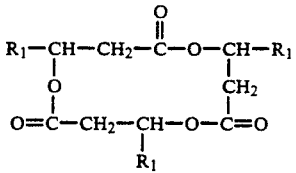
(1)

wherein $R_1$ is a $C_{1-10}$ alkyl group, which comprises cyclically trimerizing a compound of the formula (3):

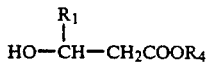
(3)

wherein $R_1$ is as defined above and $R_4$ is a $C_{1-10}$ alkyl group, by an ester exchange catalyst.

4. A cyclic compound of the formula (2):

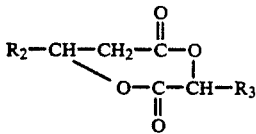
(2)

wherein $R_2$ is a $C_{1-10}$ alkyl group, and $R_3$ is a hydrogen atom or a $C_{1-10}$ alkyl group.

5. A process for producing a cyclic compound of the formula (2):

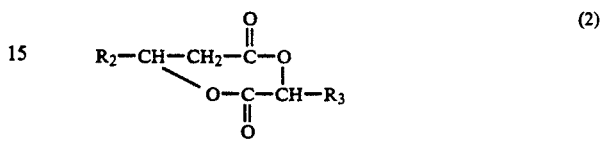
(2)

wherein $R_2$ is a $C_{1-10}$ alkyl group, and $R_3$ is a hydrogen atom or a $C_{1-10}$ alkyl group, Which comprises reacting a compound of the formula (4):

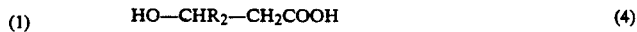
(4)

wherein $R_2$ is as defined above, with a compound of the formula (5):

$$X-CHR_3-CO-Y \qquad (5)$$

wherein $R_3$ is as defined above, and each of X and Y is a halogen atom, to form a compound of the formula (6):

(6)

wherein $R_2$, $R_3$ and X are as defined above, and then subjecting the compound of the formula (6) to a ring closure reaction.

6. The process of claim 5, wherein compounds (4) and (5) are dissolved in a solvent and reacted in the presence of an amine compound to obtain compound (6), and compound (6) is then treated with alkali to obtain compound (2) by a ring closure reaction.

* * * * *